United States Patent [19]
Fischell et al.

[11] Patent Number: 5,219,329
[45] Date of Patent: Jun. 15, 1993

[54] TWO-PIECE PERCUTANEOUS INTRODUCER SHEATH AND METHOD FOR REMOVING A THROMBUS

[75] Inventors: Robert E. Fischell, Dayton, Md.; Robert I. White, Jr., Branford, Conn.

[73] Assignee: Cathco, Inc., Dayton, Md.

[21] Appl. No.: 712,731

[22] Filed: Jun. 10, 1991

[51] Int. Cl.⁵ ..................... A61M 31/00; A61M 5/178
[52] U.S. Cl. ...................................... 604/53; 604/169; 604/249
[58] Field of Search ............... 604/158, 164, 167, 168, 604/29, 33, 35, 51, 52, 53, 175, 283, 249, 256, 169, 248

[56] References Cited

U.S. PATENT DOCUMENTS

| | | | |
|---|---|---|---|
| 2,112,629 | 3/1938 | Lloyd | 604/249 |
| 4,540,411 | 9/1985 | Bodicky | 604/169 |
| 4,613,329 | 9/1986 | Bodicky | 604/158 |

Primary Examiner—Cary E. O'Connor

[57] ABSTRACT

The two-piece percutaneous introducer sheath includes a distal portion which can remain in a blood vessel while a proximal portion can be removed after a valve at the proximal end of the distal portion is closed thus preventing undue loss of blood. Thus, a thrombus that has been pulled into the proximal portion can be removed when the proximal portion is removed without any significant blood loss after the sheath valve has been closed. Further, for any other useful therapeutic purpose, the proximal portion can be changed while the distal portion with its valve closed can remain in place in the vessel.

3 Claims, 2 Drawing Sheets

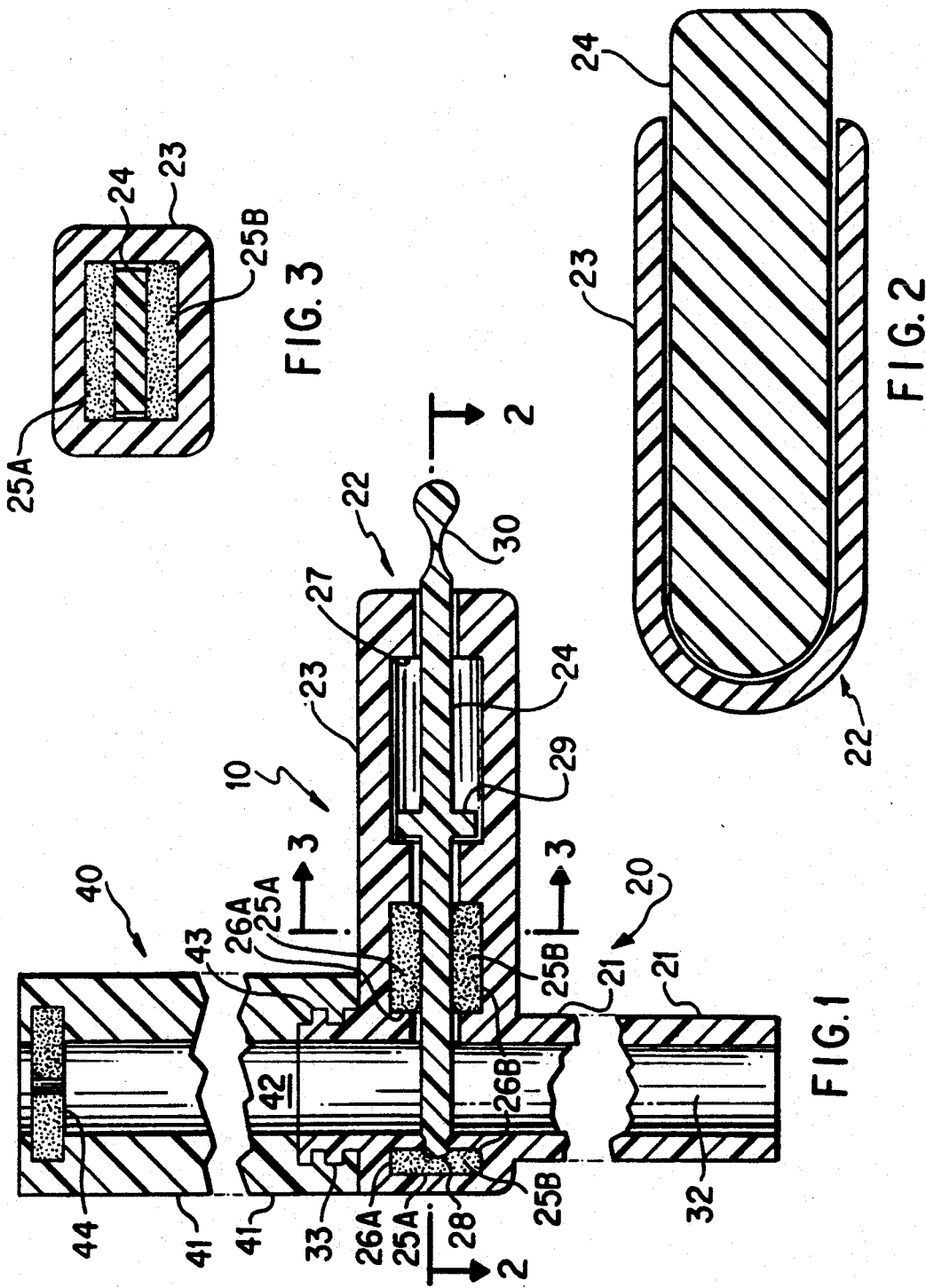

TWO-PIECE PERCUTANEOUS INTRODUCER SHEATH AND METHOD FOR REMOVING A THROMBUS

FIELD OF THE INVENTION

This invention is in the field of introducer sheaths designed to facilitate percutaneous insertion of guide wires and catheters into vessels, particularly arteries and veins of the human body.

BACKGROUND OF THE INVENTION

Introducer sheaths are frequently used to percutaneously insert guide wires, catheters and similar elongated cylinders into arteries or veins (collectively called vessels) of the human body. All such sheaths are made in one piece which precludes leaving a distal portion in the vessel while removing or changing the proximal portion that lies outside of the human body.

Furthermore, recent advances in medical techniques for removing thrombus from blood vessels involve the use of a suction catheter percutaneously inserted through an introducer sheath to hold onto a thrombus by the use of suction at the catheter's distal end. However, when the thrombus is pulled into a one-piece sheath, the valve at the sheath's proximal end must be forcibly removed before the thrombus can be pulled completely out of the sheath. This is difficult to do and typically results in considerable blood loss through the sheath's proximal end when the valve is removed.

SUMMARY OF THE INVENTION

The present invention overcomes some of the deficiencies of extant introducer sheaths in that the distal portion of the sheath can remain in a blood vessel while a proximal portion can be removed after a valve at the proximal end of the distal portion is closed thus preventing undue loss of blood. Thus, a thrombus that has been pulled into the proximal portion can be removed with the proximal portion without significant blood loss after the sheath valve has been closed. Further, for any other useful therapeutic purpose, the proximal portion can be changed while the distal portion remains in place in the vessel.

Thus, one object of this invention is to have an introducer sheath which can be percutaneously inserted into a human blood vessel and have a distal portion remain in the vessel while a proximal portion is removed.

Another object of this invention is to utilize the two-piece introducer sheath in cooperation with a percutaneously inserted suction catheter to remove thrombus from a blood vessel.

BRIEF DESCRIPTIONS OF THE DRAWINGS

FIG. 1 is a longitudinal cross section of the two-piece introducer sheath.

FIG. 2 is a longitudinal cross section of the finger operated valve of the introducer sheath taken at 2—2 of FIG. 1.

FIG. 3 is a transverse cross section of the finger operated valve taken at 3—3 of FIG. 1.

DETAILED DESCRIPTION OF THE INVENTION

Figure 4:
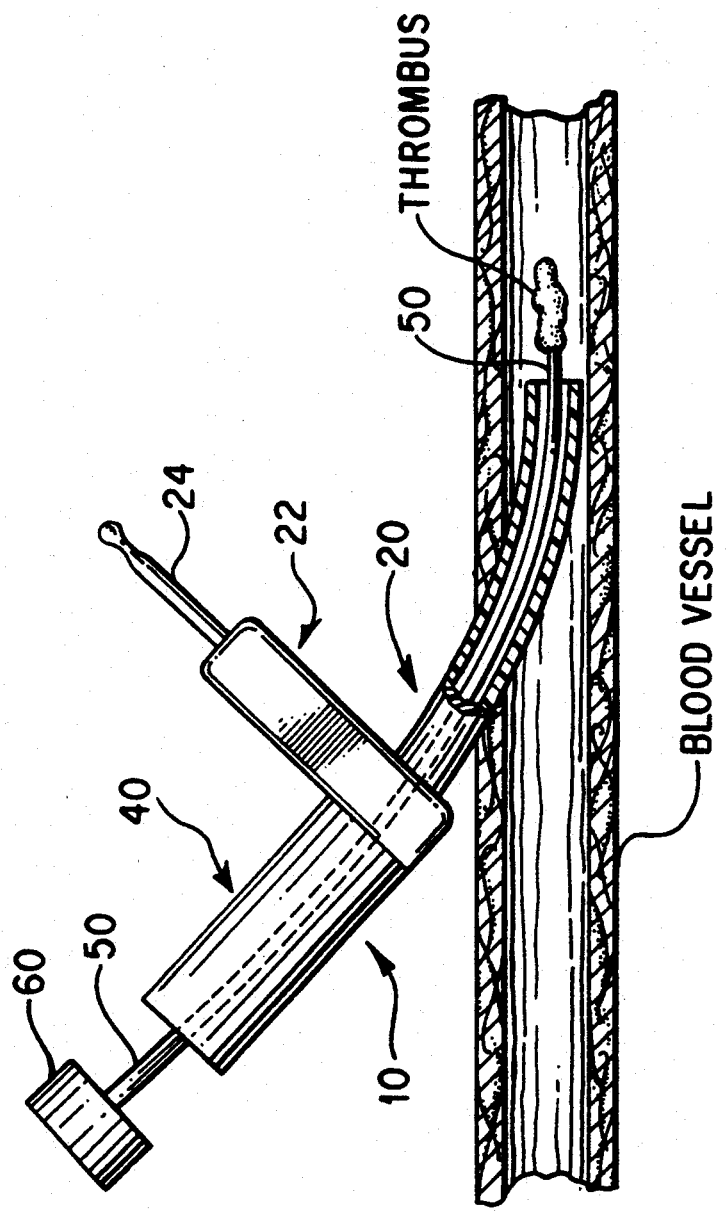
FIG. 4 is a partial longitudinal cross section of the two-piece introducer sheath illustrating the use of a suction catheter for removing thrombus from a blood vessel.

FIG. 1 shows a longitudinal cross section of the two-piece introducer sheath 10 which is formed from a distal portion 20 and a proximal portion 40. The distal portion 20 has a distal cylinder 21 which is percutaneously inserted into a blood vessel. At the proximal end of the distal portion 20 is a finger operated slide valve 22 which consists of a housing 23, a valve poppet 24 and two elastomer seals 25A and 25B. The housing 23 has cavities 26A and 26B which hold respectively the seals 25A and 25B, and an end stop 27. The poppet 24 has a tapered end 28, a poppet stop 29 and a finger grip 30. The slide valve 22 is shown in its closed position. In this position, there is no fluid communication between the lumen 32 of the distal cylinder 21 and the lumen 42 of the proximal cylinder 41 of the proximal portion 40.

In its open position (not shown) the finger grip 30 is pulled back until the poppet stop 29 of the poppet 24 makes contact with the end stop 27 of the housing 23. In its open position, the tapered end 28 is completely pulled back into the housing 23 so that there is an unobstructed lumen which joins the lumens 32 and 42 in fluid communication. The single piece upper seal 25A and the single-piece lower seal 25B are sealed respectively against the top an bottom sides of the poppet 24. This fluid seal is made whether the poppet is closed or open or at any position in between.

A male screw 33 at the proximal end of the distal portion 20 can be secured to a female nut 43 at the distal end of the proximal portion 40 to securely join together both pieces of the two-piece introducer sheath 10. The proximal portion 40 of the introducer sheath 10 can be readily removed from the percutaneously inserted distal portion 20 by unscrewing the nut 43 from the screw 33.

When the distal portion 20 is joined to the proximal portion 40, the poppet 24 would typically be in its open position, but blood does not escape through the lumens 32 and 42 because of the seal 44 at the proximal end of the proximal portion 44. When the proximal portion 40 is removed, blood leakage is prevented by closing the valve poppet 24.

Side tubes (not shown) could be joined into the cylinders 21 or 41 by conventional means if such additional access to the lumens 32 and 42 was desired.

FIG. 2 is a longitudinal cross section of the valve 22 showing the housing 23 and the poppet 24.

FIG. 3 is a transverse cross section of the valve 22 showing the housing 23, poppet 24, upper seal 25A, and the lower seal 25B.

FIG. 4 shows a method of using the two-piece introducer sheath 10 for percutaneously introducing a suction catheter 50 into a blood vessel for removing a thrombus (blood clot) from a blood vessel. As shown in FIG. 4, the distal portion 20 of the sheath 10 has been inserted into a blood vessel. A suction source 60 connected at the proximal end of the suction catheter 50 allows the distal end of the catheter 50 to hold onto a thrombus. After the thrombus is pulled completely into the proximal portion 40, the poppet 24 of the valve 22 is closed, the proximal portion 40 is unscrewed from the distal portion 20, and the suction catheter 50 with thrombus attached is completely removed from the body. After the thrombus is removed, the proximal portion 40 can be screwed back on, the slide valve 22 can be opened, the suction catheter 50 can be reinserted through the sheath 10 and the suction removal of thrombus can be accomplished additional times.

It should be understood that if the sheath was not made in two pieces, it would not be possible to remove the thrombus from the body without also removing the sheath from the body because the seal 44 at the proximal portion 40 would not allow the thrombus to pass through.

There may be other reasons beside thrombus removal for making an introducer sheath in two pieces. For example, the initial part of a procedure may require one type of proximal portion while a later or final step in the procedure might be better accomplished with a different configuration for the proximal portion.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An introducer sheath for insertion into a blood vessel of a human body comprising:
    a first and distal portion having an elongated cylindrical tube for insertion into the blood vessel and having a finger operated valve located near the proximal end of the distal portion which valve can be closed to prevent blood loss or opened to allow the passage of catheters through the central lumen of the distal portion which central lumen is of uniform internal diameter and extends freely to and through an unobstructed opening at the distal end of the distal portion;
    a second and separate proximal portion having an interior lumen which is in fluid communication with the lumen of the distal portion when the valve of the distal portion is in its open position; and
    a mechanical attachment and detachment means located at the proximal end of the distal portion and the distal end of the proximal portion for readily joining or separating the proximal portion from the distal portion.

2. The introducer sheath of claim 1 wherein the proximal portion has a seal at its proximal end.

3. A method for removing thrombus from a blood vessel comprising the steps of:
    inserting into a blood vessel a two-piece introducer sheath having a proximal portion and a separate distal portion which are mechanically joined by means by a mechanical fitting;
    opening a finger operated valve located near the proximal end of the distal portion;
    passing a suction catheter through the two-piece introducer sheath until the suction catheter's distal end is in contact with the thrombus to be removed;
    applying a suction to the suction catheter's proximal end which causes the thrombus to firmly attach to the suction catheter's distal end;
    pulling back on the suction catheter until the thrombus is located within the proximal portion of the sheath;
    closing the finger operated valve;
    disconnecting the mechanical fitting so that the proximal portion is separated from distal portion; and,
    removing the distal portion from the blood vessel.

* * * * *